United States Patent
Zeng et al.

(10) Patent No.: US 12,032,906 B2
(45) Date of Patent: Jul. 9, 2024

(54) METHOD, APPARATUS AND DEVICE FOR QUALITY CONTROL AND STORAGE MEDIUM

(71) Applicant: BEIJING BAIDU NETCOM SCIENCE AND TECHNOLOGY CO., LTD., Beijing (CN)

(72) Inventors: Qifei Zeng, Beijing (CN); Yuhong Zheng, Beijing (CN); Weijian Xu, Beijing (CN); Tao Li, Beijing (CN)

(73) Assignee: BEIJING BAIDU NETCOM SCIENCE AND TECHNOLOGY CO., LTD., Beijing (CN)

( * ) Notice: Subject to any disclaimer, the term of this patent is extended or adjusted under 35 U.S.C. 154(b) by 412 days.

(21) Appl. No.: 17/362,666

(22) Filed: Jun. 29, 2021

(65) Prior Publication Data

US 2021/0326524 A1    Oct. 21, 2021

(30) Foreign Application Priority Data

Nov. 30, 2020   (CN) .......................... 202011375351.2

(51) Int. Cl.
*G16H 10/60* (2018.01)
*G06F 40/226* (2020.01)
(Continued)

(52) U.S. Cl.
CPC .......... *G06F 40/226* (2020.01); *G06F 40/279* (2020.01); *G06N 20/00* (2019.01); *G16H 10/20* (2018.01); *G16H 10/60* (2018.01)

(58) Field of Classification Search
CPC .... G06F 40/226; G06F 40/279; G06F 40/253; G06F 16/35; G06F 16/367; G06N 20/00;
(Continued)

(56) References Cited

U.S. PATENT DOCUMENTS 9,207,760 B1 * 12/2015 Wu ..................... G06F 18/2113
2010/0191686 A1    7/2010 Wang et al.
(Continued)

FOREIGN PATENT DOCUMENTS

CN         107203600 A    9/2017
CN         109543014 A    3/2019
(Continued)

OTHER PUBLICATIONS

Wang, Answer extraction of opinions question in reading comprehension of prose for college entrance examination, Journal Zhengzhou University (Nat. Sci. Ed.) vol. 50 No. 1, Mar. 2018, 6 pages.
(Continued)

*Primary Examiner* — Pierre Louis Desir
*Assistant Examiner* — Fouzia Hye Solaiman
(74) *Attorney, Agent, or Firm* — Cozen O'Connor (57) ABSTRACT

A method, apparatus and device for quality control and storage media relate to the field of artificial intelligence technology, particularly to the field of natural language understanding and knowledge graphs, which may be applied in the medical field. The method includes: acquiring text information to be detected and domain of the text information; acquiring preset questions and machine reading comprehension model according to the domain; inputting the questions and the text information into the machine reading comprehension model to obtain extracted answers; outputting quality control information in response to the answers being not empty.

17 Claims, 5 Drawing Sheets

(51) Int. Cl.
  *G06F 40/279*  (2020.01)
  *G06N 20/00*  (2019.01)
  *G16H 10/20*  (2018.01)

(58) Field of Classification Search
  CPC .......... G06N 3/08; G06N 3/045; G06N 20/20;
        G16H 10/20; G16H 10/60; G16H 50/20;
        Y02P 90/30; G06Q 10/06395
  USPC .......................................................... 704/9
  See application file for complete search history.

(56) References Cited

U.S. PATENT DOCUMENTS

| | | | |
|---|---|---|---|
| 2017/0193095 A1* | 7/2017 | Ben-Tzur | ................ G06F 16/35 |
| 2017/0249311 A1 | 8/2017 | Pelleg et al. | |
| 2018/0181574 A1* | 6/2018 | Chen | .................. G06F 16/9535 |
| 2019/0287684 A1 | 9/2019 | Wu et al. | |
| 2019/0369957 A1 | 12/2019 | Spector et al. | |
| 2019/0371438 A1 | 12/2019 | Chintamaneni et al. | |
| 2020/0334809 A1* | 10/2020 | Vianu | ................ G06V 30/1916 |
| 2021/0304892 A1* | 9/2021 | Zheng | ...................... G06N 3/08 |
| 2021/0374576 A1* | 12/2021 | Fang | ...................... G16H 50/70 |

FOREIGN PATENT DOCUMENTS

| | | |
|---|---|---|
| CN | 110210021 A | 9/2019 |
| CN | 110675871 A | 1/2020 |
| CN | 111611391 A | 9/2020 |
| CN | 111783473 A | 10/2020 |
| GB | 2598879 A | 3/2022 |
| GB | 2614861 A | 7/2023 |
| KR | 20202268105 A | 6/2020 |

OTHER PUBLICATIONS

European Patent Application No. 21182349.7 extended European Search Report and Opinion, dated Dec. 15, 2021, 8 pages.
Yue et al., Clinical Reading Comprehension: A Thorough Analysis of the emrQA Dataset, May 1, 2020.

* cited by examiner

METHOD, APPARATUS AND DEVICE FOR QUALITY CONTROL AND STORAGE MEDIUM

CROSS-REFERENCE TO RELATED APPLICATIONS

This application claims priority to Chinese Patent Application No. 202011375351.2, filed with the China National Intellectual Property Administration (CNIPA) on Nov. 30, 2020, the contents of which are incorporated herein by reference in their entirety.

TECHNICAL FIELD

Embodiments of the present disclosure relate to the field of artificial intelligence technology, particularly to the field of natural language understanding and knowledge graphs, which may be applied in medical field.

BACKGROUND

At present, an automated quality control of electronic document (for example, medical records) is limited by the technical capabilities of traditional information manufacturers and vendors. This automated quality control usually focuses more on form (complete validity, timeliness of filling) but does not pay attention to substantial content of the document (standardized terminology, consistent expression, logical and so on). Particularly in the medical field, quality control of documents needs to rely on the hospital's three-level quality control system to conduct a large number of manual random inspections on a large number of medical record questions. Due to the limited time, manpower and capability, it is difficult to obtain an effective promotion on efficiency and quality control of the repetitive and extensive medical records.

Most of the traditional quality control algorithms are implemented based on rules, and a small part of the quality control algorithms are implemented through various models, but there is a disadvantage with these implementation methods, that is, they may not be completed with a unified method. Some methods require training a model separately for each quality control point, which will require a considerable amount of manpower and resources.

The conventional technical solution is completed based on rules and a single quality control point algorithm. For rule realization, it uses a manual rule to realize a quality control point, and a single quality control point is completed by a single algorithm, that is, one algorithm is used for a single quality control point, and there is no relationship between each quality control point.

SUMMARY

Embodiments of the present disclosure provide a method, apparatus and device for quality control. Embodiments of the present disclosure also provide a computer readable storage medium storing executable instructions for quality control.

In a first aspect, an embodiment of the present disclosure provides a method for quality control, and the method comprises: acquiring text information to be detected and domain of the text information; acquiring preset questions and machine reading comprehension model according to the domain; inputting the questions and the text information into the machine reading comprehension model to obtain extracted answers; and outputting quality control information in response to the answers being not empty.

In a second aspect, an embodiment of the present disclosure provides an apparatus for quality control, and the apparatus comprises: a text acquisition unit, configured to acquire text information to be detected and domain of the text information; a model acquisition unit, configured to acquire preset questions and machine reading comprehension model according to the domain; an extraction unit, configured to input the questions and the text information into the machine reading comprehension model to obtain the extracted answers; and an output unit, configured to output quality control information in response to the answers being not empty.

In a third aspect, an embodiment of the present disclosure provides an electronic device, and the electronic device comprises: at least one processor; and a memory communicatively connected with the at least one processor, where the memory stores instructions executable by the at least one processor, and the instructions, when executed by the at least one processor, cause the at least one processor to execute the method for quality control as described in any one of the implementations of the first aspect.

In a fourth aspect, an embodiment of the present disclosure provides a non-transitory computer readable storage medium storing computer instructions, where the computer instructions cause a computer to execute the method for quality control as described in any one of the implementations of the first aspect.

An electronic document quality control system may be constructed in a unified way according to the embodiments of the present disclosure. It is simpler to be constructed compared with the traditional methods. It only needs to mark the data and construct the corresponding questions of the quality control point. Moreover, since prior knowledge is introduced by the questions of construction, the model has better generalization ability. The quality control may be regarded as reading comprehension based on the method of reading comprehension. Each quality control point is used to answer the questions, such as whether it is consistent and what the inconsistencies are. All the quality control points are implemented in the same model.

It shall be understood that the description in this section does not intend to identify key or critical features of the embodiments of the disclosure, nor does it intend to limit the scope of the disclosure. Other features of some embodiments of the present disclosure will become readily apparent from the following description.

BRIEF DESCRIPTION OF THE DRAWINGS

The drawings intend to provide a better understanding of an embodiment of the present disclosure and are not construed as limiting the disclosure. Wherein.

DETAILED DESCRIPTION OF EMBODIMENTS

Embodiments of the present disclosure are described below in connection with the accompanying drawings, in which various details of the embodiments of the present disclosure are comprised to facilitate understanding, and are considered as example only. Accordingly, ordinary skills in the art shall recognize that various changes and modifications may be made to the embodiments described herein without departing from the scope and spirit of the present disclosure. Also, for clarity and conciseness, descriptions of well-known functions and structures are omitted from the following description.

Figure 1:
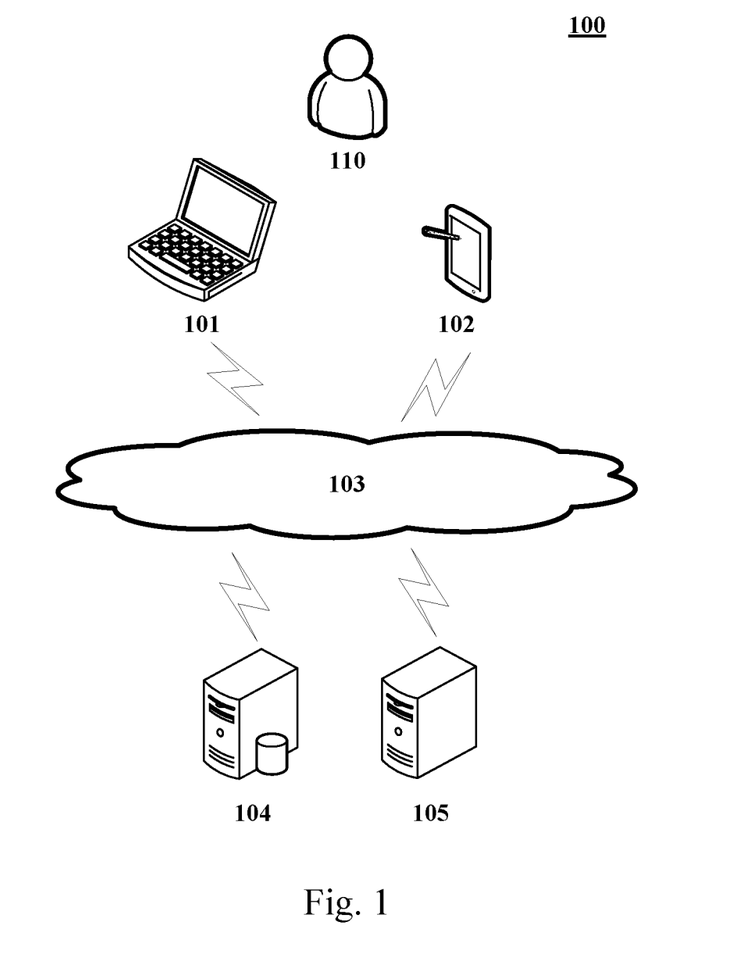
FIG. 1 is an example system architecture to which an embodiment of the present disclosure may be applied.

FIG. 1 illustrates an example system architecture 100 in which a method or an apparatus for quality control according to an embodiment of the present disclosure may be applied.

As illustrated in FIG. 1, the system architecture 100 may comprise terminal devices 101 and 102, a network 103, a database server 104 and a server 105. The network 103 serves as a medium for providing a communication link among the terminal devices 101 and 102, database server 104 and the server 105. The network 103 may comprise various types of connections, such as wired or wireless communication links, or fiber optic cables.

A user 110 may interact with the server 105 through the network 103 by using the terminal devices 101 and 102 to receive or send information, etc. Various applications may be installed on the terminal devices 101 and 102, such as model training applications, quality control applications, shopping applications, payment applications, web browsers and instant messaging tools.

The terminal devices 101 and 102 may be hardware or software. When the terminal devices 101 and 102 are hardware, they may be various electronic devices with display screens, comprising but not limited to an smart phones, tablet computers, e-book readers, MP3 players (Moving Picture Experts Group Audio Layer III), laptop portable computers and desktop computers, and the like. When the terminal devices 101 and 102 are software, they may be installed in the electronic devices listed above. They may be implemented, for example, as a plurality of software or software modules (such as for providing distributed services), or they may be implemented as a single software or software modules. It is not particularly limited herein.

When the terminal devices 101 and 102 are hardware, image capture devices may be installed on them. The image capture devices may be various devices that may realize the function of capturing images, such as cameras, sensors. The user 110 may use the image capture devices which installed on the terminal devices 101 and 102 to collect document information (for example, taking a picture of a medical record), and then recognize the content of the picture through OCR to generate an electronic document. The terminal devices 101 and 102 may also obtain electronic documents (for example, electronic medical records) directly.

The database server 104 may be a database server that provides various services. For example, a sample set may be stored in the database server. The sample set contains a large number of samples. The sample may comprise sample documents, sample questions, and sample answers. In this way, the user 110 may also select samples from the sample set stored in the database server 104 through the terminal devices 101 and 102.

The server 105 may also be a server that provides various services, for example, a background server that provides support for various applications installed on the terminal devices 101 and 102. The background server may use the samples in the sample set sent by the terminal devices 101 and 102 to train a initial model, and send the trained results (such as the generated machine reading comprehension model) to the terminal devices 101 and 102. In this way, the user may apply the generated machine reading comprehension model for quality inspection. The server may also receive the text information to be detected, use the trained machine reading comprehension model for quality inspection, and feedback the inspection results to the terminal devices.

The database server 104 and the server 105 here may also be hardware or software. When they are hardware, they may be implemented as a distributed server cluster composed of multiple servers, or as a single server. When they are software, they may be implemented as multiple software or software modules (for example, for providing distributed services), or as a single software or software module, which is not particularly limited here.

It should be noted that the method for quality control provided according to the embodiments of the present disclosure is generally executed by the server 105, and accordingly, the apparatus for quality control is generally set in the server 105.

It should be appreciated that in the case when the server 105 may implement the related functions of the database server 104, the database server 104 may not be installed in the system architecture 100.

It should be understood that the number of the terminal devices, networks and the servers in FIG. 1 is merely illustrative. There may be any number of terminal devices, networks, and servers according to actual requirements.

Figure 2:
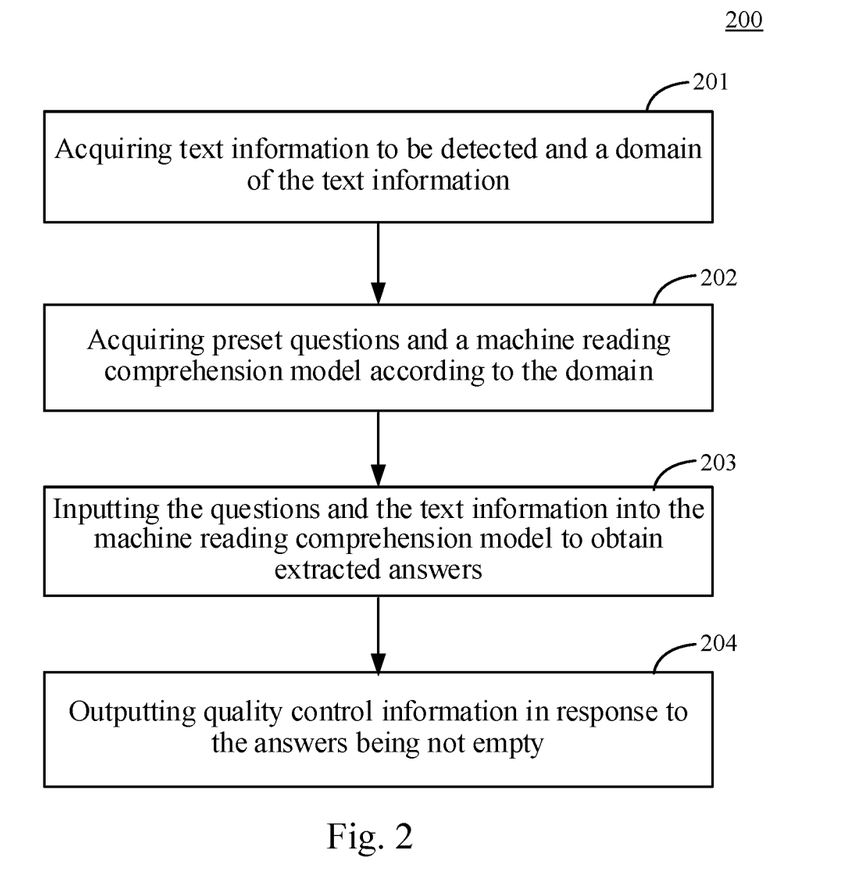
FIG. 2 is a flow chart of a method for quality control according to an embodiment of the present disclosure.

Continuing to refer to FIG. 2, a flow 200 of a method for quality control according to an embodiment of the present disclosure is illustrated. The flow 200 comprises following steps:

Step 201: acquiring text information to be detected and a domain of the text information.

In this embodiment, the execution body of the method for quality control (for example, the server 105 shown in FIG. 1) may acquire the text information to be detected and the domain of the text information in a variety of ways. For example, the execution body may acquire the text information to be detected and the domain of the text information stored in the database server (such as the database server 104 shown in FIG. 1) through a wired or a wireless connection. For another example, the execution body may also receive text information to be detected and the domain of the text information sent by terminals (such as the terminal devices 101 and 102 shown in FIG. 1). The text information may be electronic information that may be directly recognized by a computer, or may be a picture which may be translated into text through OCR (Optical Character Recognition) and other technologies. For example, the text information may be an electronic medical record or a handwritten medical record, and the handwritten medical record may be converted into an electronic medical record through a text recognition application. The domain refer to domain to which the document information belongs, such as medical, education, or sports.

Step 202: acquiring preset questions and machine reading comprehension model based on the domains.

In this embodiment, questions related to quality may be constructed in advance according to different domains. For example, a question in the medical field may be whether the symptoms of outpatient records and admission records are consistent. A question in the education field may be whether the monthly test scores fluctuate normally. The machine reading comprehension (MRC) model is a neural network model that may read documents with machine and answer related questions.

Step 203: inputting the questions and the text information into the machine reading comprehension model to obtain extracted answers.

In this embodiment, setting an article "p" and a question "q" at the same time, the purpose is to predict a "span (start, end)", where start and end are the start positions and end positions of the article "p", and the "span" is the answer to this question. The machine reading comprehension model converts this task into a binary classification problem on the sequence, that is, for each word in the article, the score of start and end are predicted respectively, and then the score is used to predict the span.

Suppose the text information is "Zhang San was born in Taiwan" and the question is "Where was Zhang San born?", after inputting the text information and the question into the machine reading comprehension model, the output label is: start [0,0,0,0,0,1,0], and end [0,0,0,0,0,0,1]. Thus, the span may be "Taiwan".

Step 204: outputting quality control information in response to the answers being not empty.

In this embodiment, if the answers to the questions are not empty, it means that a quality problem has occurred. The location of the quality control problem may be determined based on the answers, and quality control information may be output. Quality control information is used to indicate the location and category of the questions, and it may also comprise solutions (for example, who will answer the question? And what is his contact information? The combination of the questions and the answers may be pushed to the person in charge according to the contact information). For example, the question is "Which terms are not standardized?" If the answer extracted by the machine reading comprehension model is not empty, the answer is an irregular term, and the output quality control information may be "non-standard term: XXX". Alternately, the contact information of the person in charge of writing these irregular terms may be found, and the quality control information may be pushed to the person in charge. In addition, the quality control information may also be counted, such as which modules are prone to fail and how many quality control problems each responsible person has.

Quality control may be viewed as reading comprehension based on the method of reading comprehension, by the method for quality control provided in this disclosure, where each quality control point is answering the question, and all of the quality control points are implemented in the same model. Thus the efficiency of quality control is improved and the cost is reduced.

In some alternative implementations of the present embodiment, the preset questions are constructed by: acquiring a quality control requirement for the domain; regarding each field in the quality control requirement as an entity to obtain an entity set; and selecting at least one entity from the entity set and constructing the preset questions related to the selected entity according to inspection rules. For example, the requirement for quality control is to check the validity of field such as disease name and duration in the chief complaint and history of present illness in the admission record. The entity may comprise "chief complaint", "history of present illness", "name of disease", and "duration". One or more entities may be chosen to combine to construct the question. For example, a disease with a discrepancy between the "disease name" in the chief complaint and the history of present illness in the hospital admission record is searched; any illness in which the "duration" of the chief complaint is inconsistent with that of the history of present illness in the admission record is searched, then comprehensive quality control is realized according to different construct problems of quality control requirements.

Alternately, the questions may be constructed by template padding, such that the template is: [xx] of [entity 1] is inconsistent with [xx] of [entity 2]. [ ] refers to the contents filled in according to the quality control requirements, [entity 1] is the chief complaint, [entity 2] is the history of present illness, and [XX] is the duration as mentioned above.

In some alternative implementations of the present embodiment, the inspection rules comprise at least one of the following: standardization of terminology, consistency of expression, and logic. For example, the constructed questions are "Please identify the non-standard terminology in the chief complaint", "Please identify the inconsistencies between the statements in the chief complaint and history of present illness", and "Please identify the logical errors in the chief complaint and history of present illness". Thus the text information may be carried on the comprehensive inspection to obtain a better and more strict quality control.

In some alternative implementations of the present embodiment, acquiring text information to be detected and domain of the text information comprises: acquiring the text information to be detected; matching the acquired text information with preset domain keywords to determine the domain of the text information. If the domain of the text information is unknown to user in advance, the server may help to determine the domain and then invoke the corresponding machine reading comprehension model based on the domain. The domain may be determined by the method of keyword matching, through a named entity model in conventional technology and other tools to extract the keywords from the text information, and then keywords of the text information are matched with domain keywords in a preset domain keyword library, and similarity is calculated. The match is successful if the similarity is greater than a preset similarity threshold. The domain that matches successfully is the domain of text information. In this way, the machine reading comprehension model in this domain may be found accurately, and thus the quality control may be carried out after the text information is understood accurately.

Figure 3:
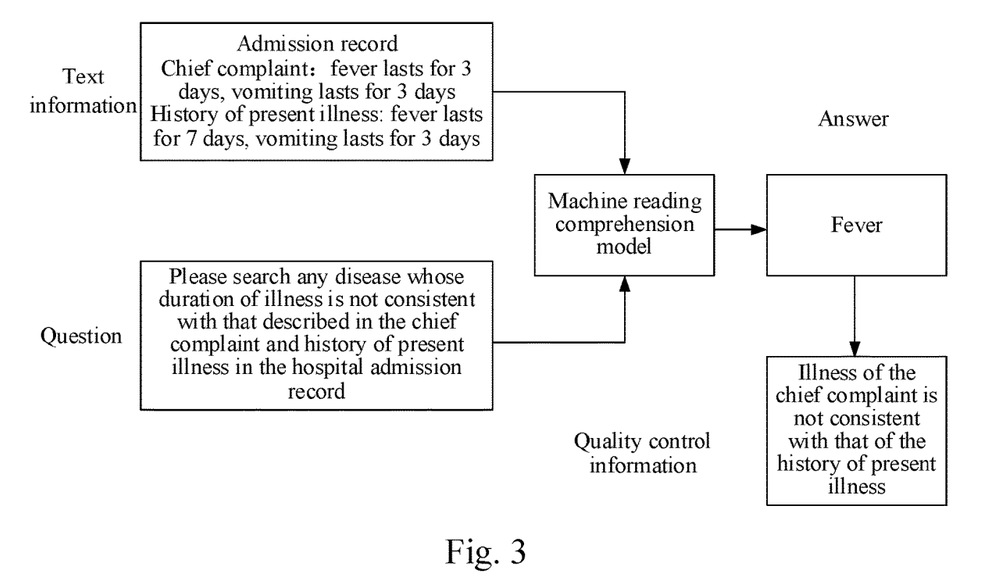
FIG. 3 is a schematic diagram of an application scenario of the method for quality control according to an embodiment of the present disclosure.

Continue to refer to FIG. 3, which is a schematic diagram of an application scenario of the method for quality control. In the application scenario of FIG. 3, applied to medical domain, the text information to be detected is "admission record, chief complaint: fever lasts for 3 days, vomiting lasts for 3 days, history of present illness: fever lasts for 7 days, vomiting lasts for 3 days". The question is "Please search any disease whose duration of illness is not consistent with that described in the chief complaint and history of present illness in the hospital admission record". The text information and questions are input into a machine reading comprehension model in the medical domain to get an answer of "Fever". In case of the answer being not empty, it indicates a quality control problem. A quality control information "illness of the chief complaint is not consistent with that of the history of present illness" may be output. Then the quality control problem may be dealt with according to the quality question in accordance with the rules and regulations.

Figure 4:
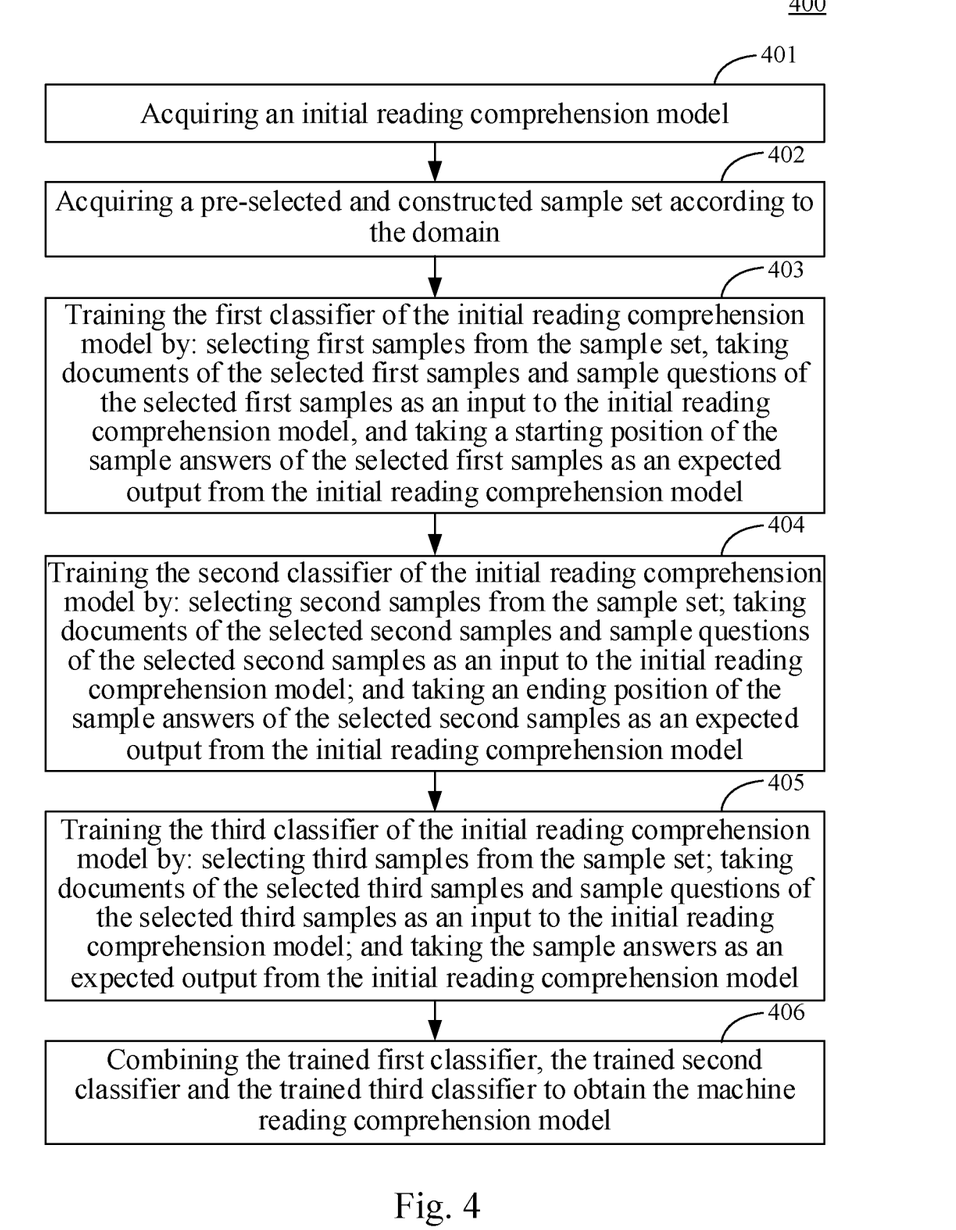
FIG. 4 is a flowchart of a method for quality control according to another embodiment of the present disclosure.

With further reference to FIG. 4, a flow 400 of a method for quality control according to another embodiment of the present disclosure is illustrated. The flow 4001 comprises the following steps:

Step 401: acquiring an initial reading comprehension model.

In this embodiment, electronic device (such as the server shown in FIG. 1) on which the method for quality control is operated may acquire an initial reading comprehension model from a third-party server. The initial reading comprehension model is a neural network model. The initial reading comprehension model comprises a first classifier, a second classifier and a third classifier. The first classifier is used to determine a starting position of the extracted answers, as is the "start" mentioned above. The second classifier is used to determine the ending position of the extracted answers, as is the "end" mentioned above. The third classifier is used to verify the validity of the answers, as is the validity of the "span" mentioned above.

Step 402: acquiring a pre-selected and constructed sample set according to the domain.

In this embodiment, the sample set comprises at least one sample, and each sample comprises documents, sample questions and sample answers. The samples are related to the domain, different domains use different samples to train domain-related machine reading comprehension models. For example, electronic medical records may be used as documentations in medical domain, questions related the quality of medical may be pre-constructed, and the answers to the questions are marked in the documents. There may be multiple answers to the same question and all the answers may be marked.

Step 403: training the first classifier of the initial reading comprehension model by: selecting first samples from the sample set, taking documents of the selected first samples and sample questions of the selected first samples as an input to the initial reading comprehension model, and taking a starting position of the sample answers of the selected first samples as an expected output from the initial reading comprehension model.

In this embodiment, the initial reading comprehension model may comprise three classifiers. The first classifier is used to determine the starting position of the extracted answers. Training for the first classifier may be done separately or in combination with multiple tasks. There may be a sharing layer (such as word embedding layer, feature extraction layer) among the first classifier, the second classifier and the third classifier to share network parameters, which may improve the convergence speed of the machine reading comprehension model. The first classifier may be an untrained deep learning model or an uncompleted trained deep learning model. Each layer of the first classifier may be set with initial parameters, which may be adjusted continuously during the training process of the first classifier. Here, the electronic device may input the documents and sample questions from the input side of the first classifier, successively go through the processing of parameters in each layer of the first classifier (such as product, convolution, etc.), and output from the output side of the first classifier. The information output from the output side is the starting position of the extracted answers. By comparing the starting position of the extracted answers with that of the sample answers, the loss value of the first classifier may be calculated according to a preset loss function. If the loss value is greater than a threshold value, the network parameters of the first classifier may be adjusted, and samples may be continued to be selected for training, otherwise the training of the first classifier is completed.

Step 404: training the second classifier of the initial reading comprehension model by: selecting second samples from the sample set, taking documents of the selected second samples and sample questions of the selected second samples as an input to the initial reading comprehension model and taking an ending position of the sample answers of the selected second samples as an expected output from the initial reading comprehension model.

In this embodiment, the second classifier is used to determine the ending position of the extracted answers. Similar to step 403, the second classifier may acquire shared parameters from the network parameters of the first classifier, to accelerate the training speed of the second classifier. The second classifier may be an untrained deep learning model or an uncompleted trained deep learning model. Each layer of the second classifier may be set with initial parameters, which may be adjusted continuously during the training process of the second classifier. Here, the electronic device may input the documents and sample questions from the input side of the second classifier, successively go through the processing of parameters in each layer of the second classifier (such as product, convolution, etc.), and output from the output side of the second classifier. The information output from the output side is the ending position of the extracted answers. By comparing the ending position of the extracted answer with that of the sample answers, the loss value of the second classifier may be calculated according to the preset loss function. If the loss value is greater than the threshold value, the network parameters of the second classifier may be adjusted, and samples may be continued to be selected for training, otherwise the training of the second classifier is completed.

Step 405: training the third classifier of the initial reading comprehension model by: selecting third samples from the sample set, taking documents of the selected third samples and sample questions of the selected third samples as an input to the initial reading comprehension model and taking the sample answers of the selected samples as an expected output from the initial reading comprehension model.

In this embodiment, the third classifier is used to verify the validity of the answers. The third classifier may be trained independently or on the basis of the first classifier and the second classifier. The third classifier may be an untrained deep learning model or an uncompleted trained deep learning model. Each layer of the third classifier may be set with initial parameters, which may be adjusted continuously during the training process of the third classifier. Here, the electronic device may input the documents and sample questions from the input side of the third classifier, successively go through the processing of parameters in each layer of the third classifier (such as product, convolution, etc.), and output from the output side of the third classifier. The information output from the output side is the extracted answers. By comparing the extracted answers with that of the sample answers, the loss value of the third classifier may be calculated according to the preset loss function. If the loss value is greater than the threshold value, the network parameters of the third classifier may be adjusted, and samples may be continued to be selected for training, otherwise the training of the third classifier is completed.

Step 406: combining the trained first classifier, the trained second classifier and the trained third classifier to obtain the machine reading comprehension model.

In this embodiment, the network layer of the first classifier, the second classifier and the third classifier with the same structure and parameters may be merged into a sharing layer, and then connected the different output layers respectively to construct a machine reading comprehension model, so that output answers is verified by the validity after the text information and questions are input into the machine reading comprehension model.

As shown in FIG. 4, compared with the corresponding embodiments in FIG. 2, flow 400 of the method for quality control in the present embodiment represents the steps to train the machine reading comprehension model. Therefore, the scheme described in the present embodiment may train machine reading comprehension model in different domains according to samples from different domains, so as to carry out quality control in a targeted way.

In some alternative implementations of the present embodiment, the method also comprises: acquiring a pre-trained model according to the domain; adjusting the parameters of the initial reading comprehension model according to the common parameters of the pre-trained model. The pre-trained model may be Bert, Ernie and other neural network models. The pre-trained model is related to the domain, and the parameters of the pre-trained model are different in different domains. Therefore, the public parameters of the pre-trained model in the same domain may be shared with the initial reading comprehension model, and the initial parameters of the initial reading comprehension model may be adjusted to be the same as the public parameters of the pre-trained model. In this way, the training speed of the machine reading comprehension model may be accelerated, the training time may be saved, and the accuracy of the machine reading comprehension model may be improved.

Figure 5:
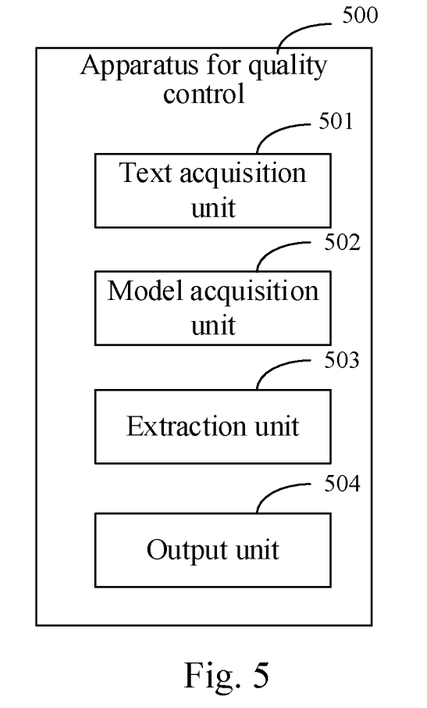
FIG. 5 is a schematic structural diagram of an apparatus for quality control according to an embodiment of the present disclosure.

With further reference to FIG. 5, as an implementation of the method shown in each of the above figures, an embodiment of the present disclosure provides an embodiment of an apparatus for quality control. The apparatus embodiment corresponds to the method embodiment shown in FIG. 2. The apparatus may be applied to various electronic equipments.

As shown in FIG. 5, the apparatus 500 for quality control in this embodiment comprises: a text acquisition unit 501, a model acquisition unit 502, an extraction unit 503, and an output unit 504. The text acquisition unit 501 is configured to acquire text information to be detected and domain of the text information. The model acquisition unit 502 is configured to acquire preset questions and machine reading comprehension model according to the domain. The extraction unit 503 is configured to input questions and text information into the machine reading comprehension model to obtain the extracted answers. The output unit 504 is configured to output quality control information in response to the answers being not empty.

In this embodiment, the particular processing of the text acquisition unit 501, the model acquisition unit 502, the extraction unit 503, and the output unit 504 of the apparatus 500 for quality control may refer to those discussed in steps 201, 202, 203 and 204 in corresponding embodiments in FIG. 2 respectively, which will not be repeated here.

In some alternative implementations of the present embodiment, the apparatus 500 also comprises a training unit (not shown) configured to: acquire an initial reading comprehension model, wherein the initial reading comprehension model comprises a first classifier, a second classifier, and a third classifier; acquire a pre-selected and constructed sample set according to the domain, wherein the sample set comprises at least one sample, and each sample comprises documents, sample questions and sample answers; Train the first classifier of the initial reading comprehension model by: selecting first samples from the sample set; taking documents of the selected first samples and sample questions of the selected first samples as an input to the initial reading comprehension model; taking a starting position of the sample answers of the selected first samples as an expected output from the initial reading comprehension model; wherein the first classifier is used to determine the starting position of the extracted answers; train the second classifier of the initial reading comprehension model by: selecting second samples from the sample set, taking documents of the selected second samples and sample questions of the selected second samples as an input to the initial reading comprehension model, and taking an ending position of the sample answers of the selected second samples as an expected output from the initial reading comprehension model, wherein the second classifier is used to determine the ending position of the extracted answers; train the third classifier of the initial reading comprehension model by: selecting third samples from the sample set, taking documents of the selected third samples and sample questions of the selected third samples as input to the model, and taking the sample answers as an expected output from the initial reading comprehension model, wherein the third classifier is used to verify the validity of the extracted answers; combining the trained first classifier, the trained second classifier and the trained third classifier to obtain the machine reading comprehension model.

In some of the alternative implementations of the present embodiment, the training unit is further configured to acquire a the pre-trained model according to the domain, and adjust the parameters of the initial reading comprehension model according to the common parameters of the pre-trained model.

In some of the alternative implementations of the present embodiment, the apparatus 500 further comprises a question building unit (not shown) configured to: acquire a quality control requirement for the domain; regard each field in the quality control requirement as an entity to obtain an entity set; and select at least one entity from the entity set and construct the preset questions related to the selected entity according to inspection rules.

In some of the alternative implementations of the present embodiment, the inspection rules comprise at least one of: standardization terminology, consistency of expression, and logic.

In some of the alternative implementations of the present embodiment, the text acquisition unit 501 is further configured to: acquire the text information to be detected; and match the acquired text information with preset domain keywords to determine the domain of the text information.

According to an embodiment of the present disclosure, the embodiment of the present disclosure further provides an electronic device and a readable storage medium.

Figure 6:
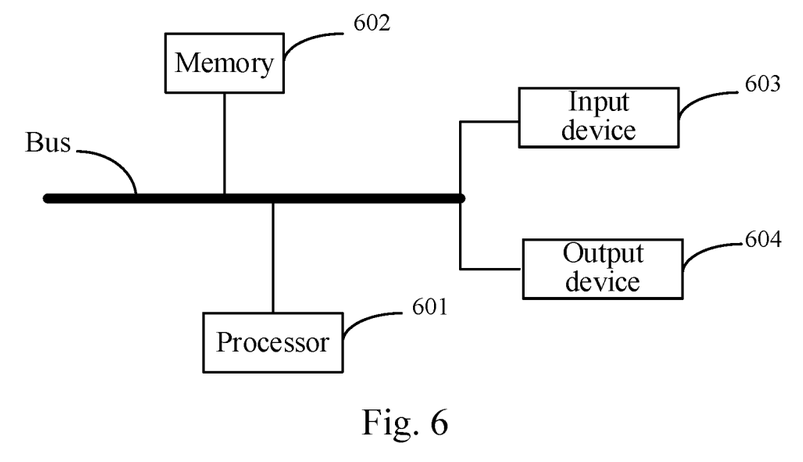
FIG. 6 is a block diagram of an electronic device used to implement the method for quality control according to an embodiment of the present disclosure.

As shown in FIG. 6, which is a block diagram of an electronic device of a method for quality control according to an embodiment of the present disclosure. The electronic device is intended to represent various forms of digital computers, such as laptop computers, desktop computers, workbenches, personal digital assistants, servers, blade servers, mainframe computers, and other suitable computers. The electronic device may also represent various forms of mobile apparatuses, such as personal digital processing, cellular phones, smart phones, wearable devices, and other similar computing apparatuses. The components shown herein, their connections and relationships, and their functions are merely examples, and are not intended to limit the implementation of an embodiment of the present disclosure described and/or claimed herein.

As shown in FIG. 6, the electronic device comprises: one or more processors 601, a memory 602, and interfaces for connecting various components, comprising high-speed interfaces and low-speed interfaces. The various components are connected to each other using different buses, and may be installed on a common motherboard or in other methods as needed. The processor may process instructions executed within the electronic device, comprising instructions stored in or on the memory to display graphic information of GUI on an external input/output apparatus (such as a display device coupled to the interface). In other embodiments, a plurality of processors and/or a plurality of buses may be used together with a plurality of memories if desired. Similarly, a plurality of electronic devices may be connected, and the devices provide some necessary operations (for example, as a server array, a set of blade servers, or a multi-processor system). In FIG. 6, one processor 601 is used as an example.

The memory 602 is a non-transitory computer readable storage medium provided by the present disclosure. The memory stores instructions executable by at least one processor, so that the at least one processor performs the method for quality control provided by the present disclosure. The non-transitory computer readable storage medium of some embodiments of the present disclosure stores computer instructions for causing a computer to perform the method for quality control provided by the present disclosure.

The memory 602, as a non-transitory computer readable storage medium, may be used to store non-transitory software programs, non-transitory computer executable programs and modules, such as program instructions/modules corresponding to the method for quality control in the embodiments of the present disclosure (for example, the text acquisition unit 501, the model acquisition unit 502, the extraction unit 503 and the output unit 504 shown in FIG. 5). The processor 601 executes the non-transitory software programs, instructions, and modules stored in the memory 602 to execute various functional applications and data processing of the server, that is, to implement the method for quality control in the foregoing method embodiment.

The memory 602 may comprise a storage program area and a storage data area, where the storage program area may store an operating system and at least one function required application program; and the storage data area may store data created by the use of the electronic device according to the method for quality control, etc. In addition, the memory 602 may comprise a high-speed random access memory, and may also comprise a non-transitory memory, such as at least one magnetic disk storage device, a flash memory device, or other non-transitory solid-state storage devices. In some embodiments, the memory 602 may optionally comprise memories remotely provided with respect to the processor 601, and these remote memories may be connected to the electronic device of the method for quality control through a network. Examples of the above network comprise but are not limited to the Internet, intranet, local area network, mobile communication network, and combinations thereof.

The electronic device of the method for quality control may further comprise: an input apparatus 603 and an output apparatus 604. The processor 601, the memory 602, the input apparatus 603, and the output apparatus 604 may be connected through a bus or in other methods. In FIG. 6, connection through a bus is used as an example.

The input apparatus 603 may receive input digital or character information, and generate key signal inputs related to user settings and function control of the electronic device of the method for quality control, such as touch screen, keypad, mouse, trackpad, touchpad, pointing stick, one or more mouse buttons, trackball, joystick and other input apparatuses. The output apparatus 604 may comprise a display device, an auxiliary lighting apparatus (for example, LED), a tactile feedback apparatus (for example, a vibration motor), and the like. The display device may comprise, but is not limited to, a liquid crystal display (LCD), a light emitting diode (LED) display, and a plasma display. In some embodiments, the display device may be a touch screen.

Various embodiments of the systems and technologies described herein may be implemented in digital electronic circuit systems, integrated circuit systems, dedicated ASICs (application specific integrated circuits), computer hardware, firmware, software, and/or combinations thereof. These various embodiments may comprise: being implemented in one or more computer programs that be executed and/or interpreted on a programmable system that comprises at least one programmable processor. The programmable processor may be a dedicated or general-purpose programmable processor, and may receive data and instructions from a storage system, at least one input apparatus, and at least one output apparatus, and transmit the data and instructions to the storage system, the at least one input apparatus, and the at least one output apparatus.

These computing programs (also referred to as programs, software, software applications, or codes) comprise machine instructions of the programmable processor and may use high-level processes and/or object-oriented programming languages, and/or assembly/machine languages to implement these computing programs. As used herein, the terms "machine readable medium" and "computer readable medium" refer to any computer program product, device, and/or apparatus (for example, magnetic disk, optical disk, memory, programmable logic apparatus (PLD)) used to provide machine instructions and/or data to the programmable processor, comprising machine readable medium that receives machine instructions as machine readable signals. The term "machine readable signal" refers to any signal used to provide machine instructions and/or data to the programmable processor.

In order to provide interaction with a user, the systems and technologies described herein may be implemented on a computer, the computer has: a display apparatus for displaying information to the user (for example, CRT (cathode ray tube) or LCD (liquid crystal display) monitor); and a keyboard and a pointing apparatus (for example, mouse or trackball), and the user may use the keyboard and the pointing apparatus to provide input to the computer. Other types of apparatuses may also be used to provide interaction with the user; for example, feedback provided to the user may be any form of sensory feedback (for example, visual feedback, auditory feedback, or tactile feedback); and any form (comprising acoustic input, voice input, or tactile input) may be used to receive input from the user.

The systems and technologies described herein may be implemented in a computing system that comprises backend components (e.g., as a data server), or a computing system that comprises middleware components (e.g., application server), or a computing system that comprises frontend components (for example, a user computer having a graphical user interface or a web browser, through which the user may interact with the implementations of the systems and the technologies described herein), or a computing system that comprises any combination of such backend components, middleware components, or frontend components. The components of the system may be interconnected by any form or medium of digital data communication (e.g., communication network). Examples of the communication network comprise: local area networks (LAN), wide area networks (WAN), and the Internet.

The computer system may comprise a client and a server. The client and the server are generally far from each other and usually interact through the communication network. The relationship between the client and the server is generated by computer programs that run on the corresponding computer and have a client-server relationship with each other. The server may be a server of distributed systems, or a server combined with a blockchain. The server may also be a cloud server, or a smart cloud computing server or smart cloud host with artificial intelligence technology.

A quality control system in different domains may be constructed in a unified way according to the technical solutions of the embodiments of the present disclosure. It is simpler to be constructed compared with the traditional methods. It only needs to mark the data and construct the corresponding questions of the quality control point. Moreover, since prior knowledge is introduced by the questions of construction, the model has better generalization ability. The quality control may be regarded as reading comprehension based on the method of reading comprehension. Each quality control point is used to answer the questions, such as whether they are consistent and what the inconsistencies are. All the quality control points are implemented in the same model.

It should be understood that the various forms of processes shown above may be used to reorder, add, or delete steps. For example, the steps described in the present disclosure may be performed in parallel, sequentially, or in different orders. As long as the desired results of the technical solution disclosed in the present disclosure be achieved, no limitation is made herein.

The above particular embodiments do not constitute limitation on the protection scope of the present disclosure. Those skilled in the art should understand that various modifications, combinations, sub-combinations and substitutions may be made according to design requirements and other factors. Any modification, equivalent replacement and improvement made within the spirit and principle of the present disclosure shall be comprised in the protection scope of the present disclosure.

What is claimed is:

1. A method for quality control, comprising:
    acquiring text information to be detected and a domain of the text information;
    acquiring preset questions and a machine reading comprehension model according to the domain;
    inputting the questions and the text information into the machine reading comprehension model to obtain extracted answers; and
    outputting quality control information in response to the answers being not empty;
    wherein the machine reading comprehension model is trained by:
        acquiring an initial reading comprehension model, wherein the initial reading comprehension model comprises a first classifier, a second classifier and a third classifier;
        acquiring a pre-selected and constructed sample set according to the domain, wherein the sample set comprises at least one sample comprising documents, sample questions and sample answers;
        training the first classifier of the initial reading comprehension model by:
            selecting first samples from the sample set
            taking documents of the selected first samples and sample questions of the
        selected first samples as an input to the initial reading comprehension model; and
            taking a starting position of the sample answers of the selected first samples as an expected output from the initial reading comprehension model;
            wherein the first classifier is used to determine the starting position of the extracted answers;
        training the second classifier of the initial reading comprehension model by:
            selecting second samples from the sample set
            taking documents of the selected second samples and sample questions of the selected second samples as an input to the initial reading comprehension model; and
            taking an ending position of the sample answers of the selected second samples as an expected output from the initial reading comprehension model;
            wherein the second classifier is used to determine the ending position of the extracted answers;
        training the third classifier of the initial reading comprehension model by:
            selecting third samples from the sample set
            taking documents of the selected third samples and sample questions of the selected third samples as an input to the initial reading comprehension model; and
            taking the sample answers as an expected output from the initial reading comprehension model;
            wherein the third classifier is used to verify validity of the extracted answers; and
        combining the trained first classifier, the trained second classifier and the trained third classifier to obtain the machine reading comprehension model.

2. The method according to claim 1, wherein the method further comprises:
    acquiring a pre-trained model according to the domain; and
    adjusting parameters of the initial reading comprehension model according to common parameters of the pre-trained model.

3. The method according to claim 2, wherein acquiring the text information to be detected and the domain of the text information comprises:
    acquiring the text information to be detected; and
    matching the acquired text information with preset domain keywords to determine the domain of the text information.

4. The method according to claim 1, wherein the preset questions are constructed by:
    acquiring a quality control requirement for the domain;
    regarding each field in the quality control requirement as an entity to obtain an entity set; and
    selecting at least one entity from the entity set and constructing the preset questions related to the selected entity according to inspection rules.

5. The method according to claim 4, wherein the inspection rules comprise at least one of: standardization terminology, consistency of expression, or logic.

6. The method according to claim 5, wherein acquiring the text information to be detected and the domain of the text information comprises:
acquiring the text information to be detected; and
matching the acquired text information with preset domain keywords to determine the domain of the text information.

7. The method according to claim 4, wherein acquiring the text information to be detected and the domain of the text information comprises:
acquiring the text information to be detected; and
matching the acquired text information with preset domain keywords to determine the domain of the text information.

8. The method according to claim 1, wherein acquiring the text information to be detected and the domain of the text information comprises:
acquiring the text information to be detected; and
matching the acquired text information with preset domain keywords to determine the domain of the text information.

9. The method according to claim 1, wherein acquiring the text information to be detected and the domain of the text information comprises:
acquiring the text information to be detected; and
matching the acquired text information with preset domain keywords to determine the domain of the text information.

10. An electronic device, comprising:
at least one processor; and
a memory, communicated with the at least one processor,
wherein the memory stores an instruction executable by the at least one processor, and the instruction is executed by the at least one processor, to enable the at least one processor to perform an operation for processing information, comprising:
acquiring text information to be detected and a domain of the text information;
acquiring preset questions and a machine reading comprehension model according to the domain;
inputting the questions and the text information into the machine reading comprehension model to obtain extracted answers; and
outputting quality control information in response to the answers being not empty,
wherein the machine reading comprehension model is trained by:
acquiring an initial reading comprehension model, wherein the initial reading comprehension model comprises a first classifier, a second classifier and a third classifier;
acquiring a pre-selected and constructed sample set according to the domain, wherein the sample set comprises at least one sample comprising documents, sample questions and sample answers;
training the first classifier of the initial reading comprehension model by:
selecting first samples from the sample set
taking documents of the selected first samples and sample questions of the selected first samples as an input to the initial reading comprehension model; and
taking a starting position of the sample answers of the selected first samples as an expected output from the initial reading comprehension model;
wherein the first classifier is used to determine the starting position of the extracted answers;
training the second classifier of the initial reading comprehension model by:
selecting second samples from the sample set
taking documents of the selected second samples and sample questions of the selected second samples as an input to the initial reading comprehension model; and
taking an ending position of the sample answers of the selected second samples as an expected output from the initial reading comprehension model;
wherein the second classifier is used to determine the ending position of the extracted answers;
training the third classifier of the initial reading comprehension model by:
selecting third samples from the sample set
taking documents of the selected third samples and sample questions of the selected third samples as an input to the initial reading comprehension model; and
taking the sample answers as an expected output from the initial reading comprehension model;
wherein the third classifier is used to verify validity of the extracted answers; and
combining the trained first classifier, the trained second classifier and the trained third classifier to obtain the machine reading comprehension model.

11. The device according to claim 10, wherein the method further comprises:
acquiring a pre-trained model according to the domain; and
adjusting parameters of the initial reading comprehension model according to common parameters of the pre-trained model.

12. The device according to claim 11, wherein acquiring the text information to be detected and the domain of the text information comprises:
acquiring the text information to be detected; and
matching the acquired text information with preset domain keywords to determine the domain of the text information.

13. The device according to claim 10, wherein the preset questions are constructed by:
acquiring a quality control requirement for the domain;
regarding each field in the quality control requirement as an entity to obtain an entity set; and
selecting at least one entity from the entity set and constructing the preset questions related to the selected entity according to inspection rules.

14. The device according to claim 13, wherein the inspection rules comprise at least one of: standardization terminology, consistency of expression, and logic.

15. The device according to claim 13, wherein acquiring the text information to be detected and the domain of the text information comprises:
acquiring the text information to be detected; and
matching the acquired text information with preset domain keywords to determine the domain of the text information.

16. The device according to claim 10, wherein acquiring text information to be detected and a domain of the text information comprises:
acquiring the text information to be detected; and
matching the acquired text information with preset domain keywords to determine the domain of the text information.

17. The device according to claim 10, wherein acquiring the text information to be detected and the domain of the text information comprises:
acquiring the text information to be detected; and matching the acquired text information with preset domain keywords to determine the domain of the text information.

* * * * *